US008983581B2

(12) United States Patent  (10) Patent No.: US 8,983,581 B2
Bawendi et al.  (45) Date of Patent: Mar. 17, 2015

(54) SYSTEM AND METHOD FOR LARGE FIELD OF VIEW, SINGLE CELL ANALYSIS

(75) Inventors: Moungi G. Bawendi, Cambridge, MA (US); Jorge M. Ferrer, Cambridge, MA (US); W. David Lee, Brookline, MA (US); Lisa F. Marshall, Cambridge, MA (US); David G. Kirsch, Durham, NC (US)

(73) Assignees: Massachusetts Institute of Technology, Cambridge, MA (US); Duke University, Durham, NC (US)

( * ) Notice: Subject to any disclaimer, the term of this patent is extended or adjusted under 35 U.S.C. 154(b) by 987 days.

(21) Appl. No.: 12/469,395

(22) Filed: May 20, 2009

(65) Prior Publication Data

US 2009/0299196 A1  Dec. 3, 2009

Related U.S. Application Data

(60) Provisional application No. 61/128,838, filed on May 27, 2008.

(51) Int. Cl.
*A61B 6/00* (2006.01)
*G06K 9/00* (2006.01)
*A61B 5/00* (2006.01)

(52) U.S. Cl.
CPC .............. *A61B 5/0071* (2013.01); *A61B 5/0084* (2013.01)
USPC ............................. 600/476; 600/473; 382/128

(58) Field of Classification Search
USPC .............................. 600/473, 476, 478; 424/9.1
See application file for complete search history.

(56) References Cited

U.S. PATENT DOCUMENTS

| | | | | |
|---|---|---|---|---|
| 5,438,989 | A * | 8/1995 | Hochman et al. | 600/426 |
| 5,688,221 | A * | 11/1997 | Yabe et al. | 600/121 |
| 5,769,791 | A * | 6/1998 | Benaron et al. | 600/473 |
| 6,256,530 | B1 * | 7/2001 | Wolfe | 600/477 |
| 6,620,621 | B1 * | 9/2003 | Cohenford et al. | 436/63 |
| 6,631,230 | B1 * | 10/2003 | Campbell | 385/121 |
| 6,667,159 | B1 * | 12/2003 | Walt et al. | 435/7.32 |
| 6,834,238 | B1 * | 12/2004 | Hochman | 702/21 |
| 7,128,894 | B1 | 10/2006 | Tannous et al. | |
| 7,285,089 | B2 * | 10/2007 | Viellerobe et al. | 600/168 |
| 7,383,077 | B2 * | 6/2008 | Zeng | 600/473 |
| 7,452,727 | B2 | 11/2008 | Hennig et al. | |
| 2002/0165456 | A1 | 11/2002 | Canpolat et al. | |
| 2003/0039741 | A1 | 2/2003 | Carver et al. | |
| 2003/0138378 | A1 | 7/2003 | Hashimshony | |
| 2004/0071332 | A1 * | 4/2004 | Bruce et al. | 382/133 |
| 2005/0207668 | A1 | 9/2005 | Perchant et al. | |
| 2006/0188797 | A1 * | 8/2006 | Roy et al. | 430/30 |
| 2006/0253107 | A1 | 11/2006 | Hashimshony et al. | |

(Continued)

*Primary Examiner* — Katherine Fernandez
(74) *Attorney, Agent, or Firm* — Quarles & Brady, LLP

(57) ABSTRACT

A method and system for medical imaging employs an excitation source configured to cause an object having a plurality of cells to at least one of emit, reflect, and fluoresce light. An optical receptor is employed that is configured to receive the light from the object. A filter assembly receives the light from the optical receptor and filters the light. An image processor having a field of view (FOV) substantially greater than a diameter of a cell of the object and an analysis resolution substantially matched to the diameter of a cell of the object that receives the filtered light from the filter and analyzes the filtered light corresponding to each cell in the FOV. A feedback system is provided that is configured to provide an indication of a state of each cell in the FOV and a location of a cell in the FOV meeting a predetermined condition.

29 Claims, 13 Drawing Sheets

(56) References Cited

U.S. PATENT DOCUMENTS

| | | |
|---|---|---|
| 2007/0160279 A1 | 7/2007 | Demos |
| 2007/0182959 A1* | 8/2007 | Maier et al. .................. 356/301 |
| 2007/0255169 A1 | 11/2007 | Hashimshony et al. |
| 2007/0260156 A1 | 11/2007 | Hashimshony |
| 2008/0015446 A1 | 1/2008 | Mahmood et al. |
| 2008/0029711 A1 | 2/2008 | Viellerobe et al. |
| 2008/0039742 A1 | 2/2008 | Hashimshony et al. |
| 2008/0103373 A1* | 5/2008 | Matter et al. .................. 600/306 |
| 2008/0154102 A1 | 6/2008 | Frangioni et al. |
| 2008/0287750 A1 | 11/2008 | Hashimshony et al. |

* cited by examiner

SYSTEM AND METHOD FOR LARGE FIELD OF VIEW, SINGLE CELL ANALYSIS

CROSS-REFERENCE TO RELATED APPLICATIONS

The application is based on, claims the benefit of, and incorporates by reference U.S. Provisional Application Ser. No. 61/128,838, filed May 27, 2008, and entitled "LARGE OPTICAL FIELD INDIVIDUAL CELL ASSAY."

STATEMENT REGARDING FEDERALLY SPONSORED RESEARCH

N/A

BACKGROUND

The present invention relates generally to a medical device and more particularly to an apparatus for intra-operative examination of tissue and identification of target cells in-vivo.

During surgical operations to remove cancerous tumors, one of the greatest areas of uncertainty lies in determining whether all of the cancerous cells at the periphery of a tumor have been removed. Current standards of care call for the removal of all cancerous tissue by removing a surrounding layer of healthy tissue. That is, current standards of care call for the resection of more tissue than believed necessary to remove the cancer. This "extra" layer of healthy tissue is referred to as a "healthy margin" and can range from a single cell to 10 mm or more in depth.

After the tumor with its margin has been removed, the tissue is sent post-operatively to a pathologist for in-vitro examination of the margin. The pathologist examines multiple representative points along the margin to assess whether cancerous cells exist at the edge of the excised tissue. That is, the pathologist attempts to determine whether the margin contains cancerous cells. Thus, the pathologist conducts a cellular-level review of the excised tissue to determine if the tissue within the margin includes cancer cells. If cancer cells are found at or close to the surface of the specimen, re-excision is often recommended and the patient must undergo a second surgical procedure when possible.

Even where the pathologist determines that the margin is clean, patients may still undergo forms of post-surgical therapy to the tumor bed due to the fact that the in-vitro analysis of the tissue cannot definitively determine if all cancer cells surrounding the cancer were removed. For example, it is not uncommon for the margin to be damaged, such as by staples or other devices used during the resection. In these cases, it may be difficult to properly analyze the margin. As such, the standard of care often dictates that the patient receive post-surgical therapy, such as radiological therapy, which has a high cost and, in and of itself, has detrimental health effects. It is estimated that at least two-thirds of all cancer patients have all cancer cells removed during an operation, yet most cancer patients receive radiation therapy post-operation. Many of these patients may be spared this treatment if it was more definitively known whether all of the cancerous cells were removed during surgery.

Thus, in-vitro pathological analysis has a number of advantages and disadvantages. Advantageously, in-vitro pathological analysis allows for a careful, cellular-level analysis of tissue in a controlled environment. Unfortunately, to provide these advantages, "extra" tissue must be removed and, because this analysis is of cells removed from the body instead of the cells remaining in the body, at best, the analysis provides an indication of what may be present in the body. That is, the in-vitro analysis cannot provide a definitive answer of whether all cancer cells were removed and, often, subsequent surgeries and/or radiation therapy is dictated by the standard of care.

As such, extensive research has been directed towards methods of reducing the uncertainty in tumor removal through in-vivo examination of the removal site or the excised tissue. As will be described, a variety of systems and methods have been developed to analyze tissue in vivo; however, as will be described, each is plagued by its own set of disadvantages.

Some in-vivo examination systems use optically-based molecular probes. These optical probes emit light when interacting with a target cell. Such probes can be fluorophores, luciferase, fluorescence resonance energy transfer (FRET) between chromophores, quantum dots, or dyes. To reach the single-cell analysis level, much like the in-vitro process described above, a form of microscopy or optical magnification is employed. While exhibiting a high degree of sensitivity, such detectors are difficult to use in-vivo. In order to detect single cells on the order of, for example, 20 microns, both the field of view (FOV) and depth of field of these detectors are typically constrained to tens of microns. These technologies, therefore, are not suited for scanning for a small number of cells over a relatively large area, such as a centimeter. For example, some in-vivo optical probe visualization systems have used a fiber-optic-coupled confocal microscope, such as the Cellvizio system. Cellvizio is a registered trademark of Mauna Kea Technologies of France. While able to achieve single-cell resolution during an in-vivo examination, the FOV of such microscopes is limited to 0.2 mm. Others have attempted to use an optical catheter with a 460 micron FOV and pneumatically adjustable focal point with a nominal 26 micron focal distance adjustable mechanically up to 200 microns. However, this device is similarly limited by its small FOV.

While microscopes having greater focal planes can be employed, the depth of field is still narrow and the microscopes require that a fixed distance is maintained between the lens and the cells of interest. Thus, these systems, generally, are not feasible for a definitive analysis of tissue in-vivo due to natural motions, such as blood flow, small muscle movement, breathing, and the like. That is, unlike the controlled environment of a pathology laboratory, microscope-based analysis tools are generally found to be unsuitable for use in-vivo to analyze the results of surgical procedures due to the natural interference with cellular analysis presented by fluids, motion, and the like. Hence, at best, such systems can be used to attempt to gain some in-vivo information, but in-vitro analysis of a margin is still required.

Beyond optical imaging, other detection techniques include nuclear magnetic resonance (NMR) with magnetic nano-particle probes and in-cell NMR with isotopes of nitrogen and carbon. However, the sensitivity of nano-particle NMR techniques is on the order of millimeters and, therefore, this technology can not detect at the single-cell level. While in-cell isotope tagged NMR is more sensitive, the resolution is still only several hundred cells in-vitro. Thus, like microscope- or magnification-based, in-vivo analysis tools, such systems are only suitable for attempting to gain some in-vivo information, but in-vitro analysis of a margin is still required.

Some have attempted to use other analytical mechanisms than optical analysis or NMR analysis. For example, some have attempted to use the electrical and/or electro-magnetic properties of cells to determine a given cell is cancerous. In these systems, a probe is used to analyze the patient's tissue following resection. Advantageously, these systems allow for in-vivo analysis of a sufficiently large analysis area and can be properly utilized in the presence of fluids, motion, and the like. Unfortunately, they do not provide for individual, cellular analysis and have varying and/or limited analytical depths. Also, unlike optical- or NMR-based systems that allow for direct, cellular analysis, these probes rely on an indirect analysis of cells through the electrical properties of the cell. Thus, they do not provide for sufficiently definitive analysis to conclude that all cancer cells have been removed.

Therefore, it would be desirable to have a system and method for in-vivo analysis of tissue that is capable of analyzing a substantially large volume of tissue with sufficient accuracy to provide clinical certainty of tissue pathology.

SUMMARY

The present invention overcomes the aforementioned drawbacks by providing a system and method for analyzing tissue in-vivo using a field of view (FOV) substantially greater than a diameter of a cell of an object, but an analysis resolution substantially matched to the diameter of a cell of the object. By way of example and not limitation, the disclosed system can be used to intra-operatively identify residual malignant cells after a tumor has been resected, allowing surgeons to excise the malignant cells before the patient leaves the operating room Furthermore, the assurance that there are no residual cancer cells can spare a given patient unnecessary post-operation radiation therapy and the associated morbidity and cost. The presented device additionally enables areas with residual cells, cancerous or otherwise, to be marked with surgical clips or other means when removal is not practical, thereby allowing focused post-operative radiation treatment.

In accordance with one aspect of the present invention, a medical imaging system is disclosed that includes an excitation source configured to cause an object having a plurality of cells to emit, reflect, or fluoresce light. The system includes an optical receptor configured to receive the light from the object and a filter assembly configured to receive the light from the optical receptor and filter the light. The system also includes an image processor having a field of view (FOV) substantially greater than a diameter of a cell of the object and an analysis resolution substantially matched to the diameter of a cell of the object and configured to receive the filtered light from the filter and analyze the filtered light corresponding to each cell in the FOV. Also, the system includes a feedback system configured to provide an indication of a state of each cell in the FOV and a location of a cell in the FOV meeting a predetermined condition.

In accordance with another aspect of the present invention, a medical imaging system is disclosed that includes an excitation light source having configured to cause an object having a plurality of cells to emit, reflect, or fluoresce. The system includes an optical fiber bundle configured to receive light from a cell of the object, where each optical fiber in the bundle is configured to receive light from substantially one cell of the object. The system also includes an image processor having a field of view (FOV) substantially greater than a diameter of a cell of the object and an analysis resolution substantially matched to a size of an optical fiber in the optical fiber bundle and configured to receive the light from the optical fiber bundle and analyze the light. A feedback system is configured to provide an indication of a state of each cell in the FOV and a location of a cell in the FOV meeting a predetermined condition.

The foregoing and other advantages of the inventions will appear in the detailed description that follows. In the description, reference is made to the accompanying drawings.

BRIEF DESCRIPTION OF THE DRAWINGS

Implementations of the invention will become more apparent from the detailed description set forth below when taken in conjunction with the drawings, in which like elements bear like reference numerals.

DETAILED DESCRIPTION

The steps, methods, processes, and devices described in connection with the implementations disclosed herein, are made with reference to the Figures, in which like numerals represent the same or similar elements. While described in terms of the best mode, it will be appreciated by those skilled in the art that the description is intended to cover alternatives, modifications, and equivalents as may be included within the spirit and scope of the invention as defined by the appended claims and their equivalents as supported by the following disclosure and drawings. Reference throughout this specification to "one implementation," "an implementation," or similar language means that a particular feature, structure, or characteristic described in connection with the implementation is included in at least one implementation of the present invention. Thus, appearances of the phrases "in one implementation," "in an implementation," and similar language throughout this specification may, but do not necessarily, all refer to the same implementation.

The described features, structures, or characteristics of the invention may be combined in any suitable manner in one or more implementations. In the following description, numerous specific details are recited to provide a thorough understanding of implementations of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

The schematic flow charts included are generally set forth as logical flow chart diagrams. As such, the depicted order and labeled steps are indicative of one implementation of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

Figure 1:
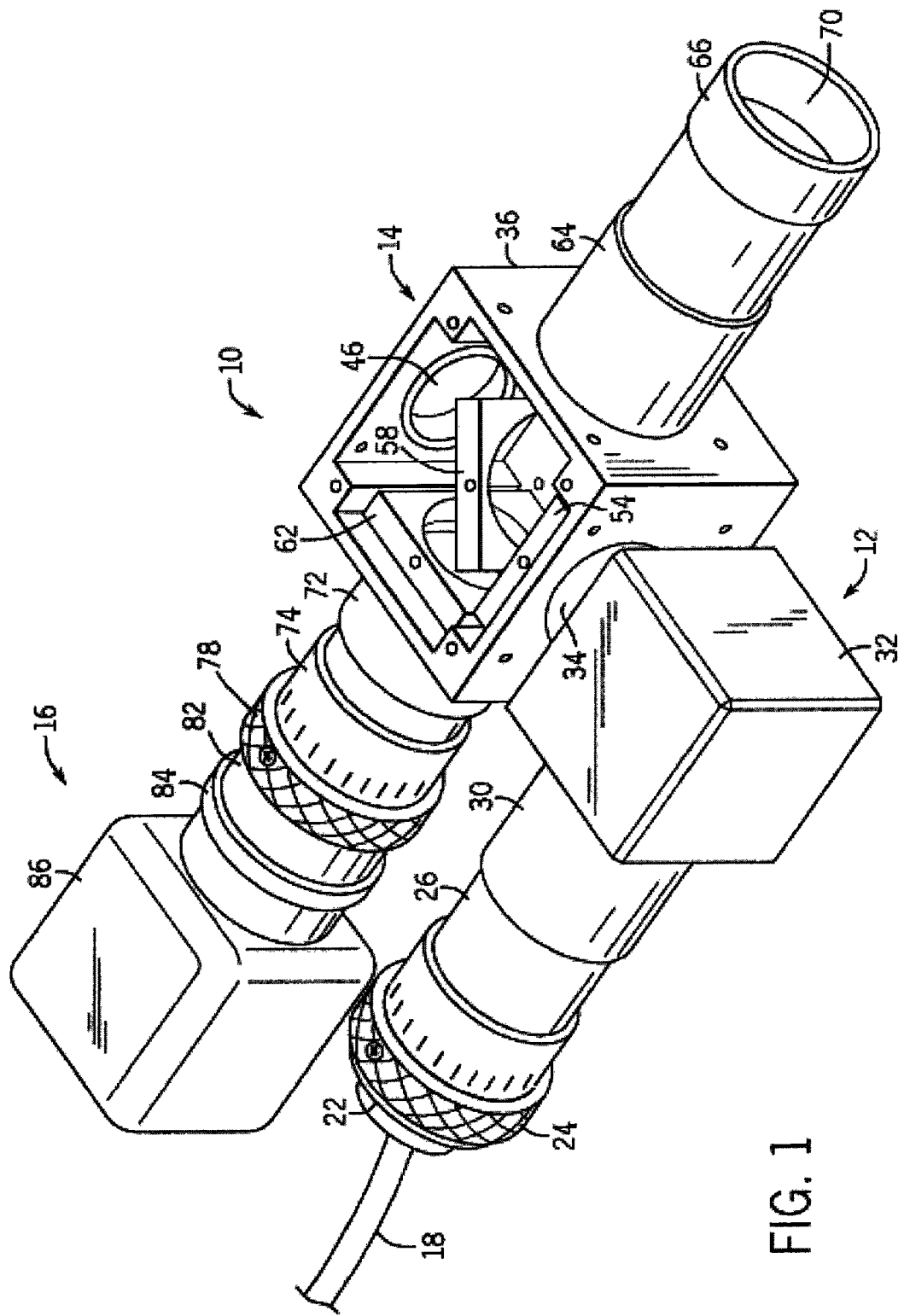
FIG. 1 is a perspective view of an exemplary device according to the present disclosure.
Figure 2:
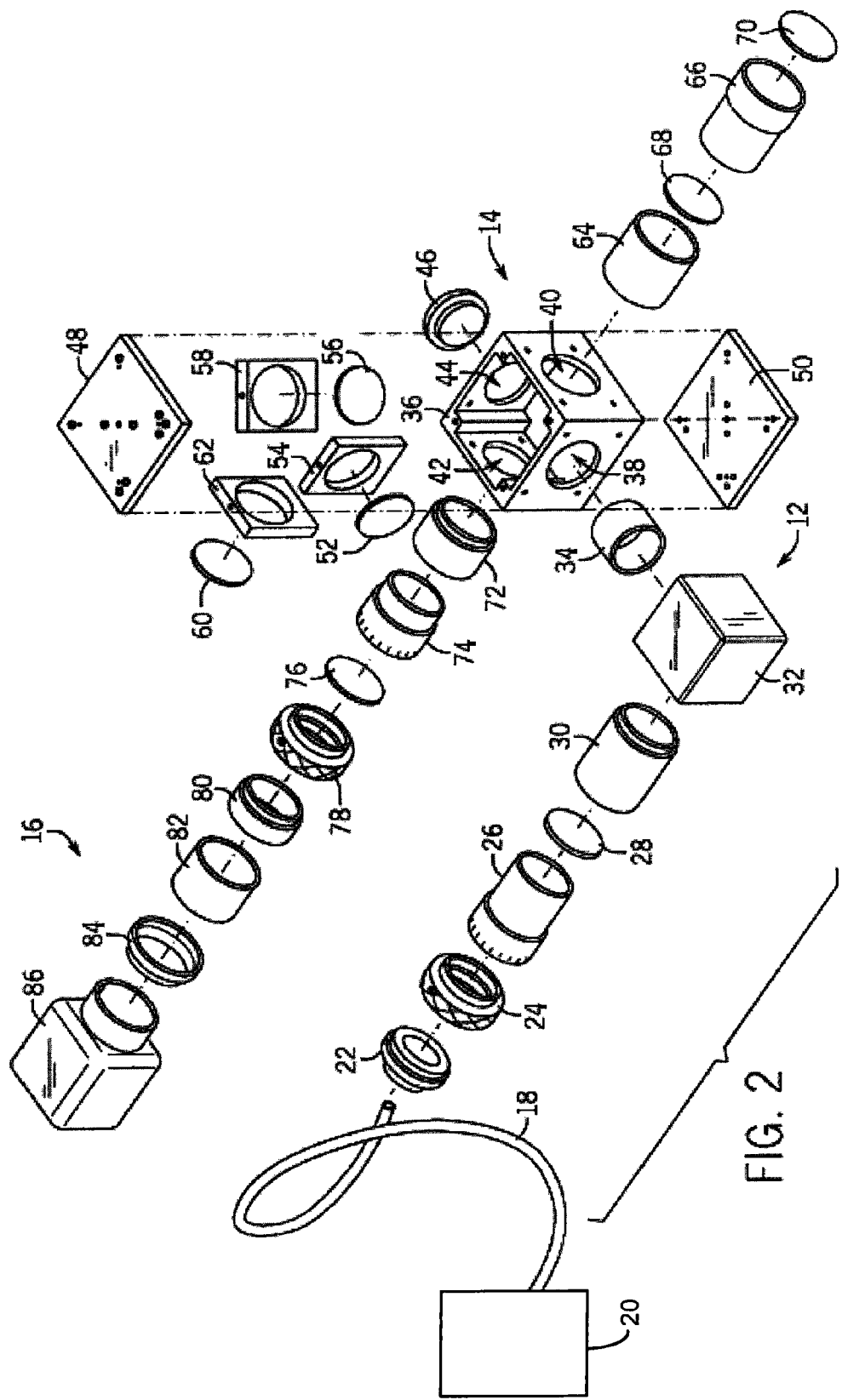
FIG. 2 is an exploded view of the exemplary device of FIG. 1.

Referring to FIGS. 1 and 2, a medical device 10 is provided that includes an excitation assembly 12, a filter assembly 14, and an image capturing device 16. The excitation assembly 12 includes an excitation fiber bundle 18 that extends from an excitation source 20 to a fiber adapter 22 and iris 24. As will be explained, the excitation source may be a lamp, a laser, or other source of photons and may be white light or have a specific wavelength within and/or outside of the visible spectrum. As discussed, in certain implementations, the excitation source 20 is located remotely and, thus, the excitation fiber bundle 18 carries excitation light from the excitation source 20 to the fiber adapter 22. In other implementations, the excitation source 20 may be attached to the iris 24 through an adapter and, therefore, the excitation fiber bundle 18 is unnecessary. In yet other implementations, the excitation source may not be necessary or may be separated from the imaging assembly 16 and filter assembly 14.

In any case, in the illustrated configuration, the fiber adapter 22 couples the excitation fiber bundle 18 to the iris 24, which is connected through a first spacer 26 to a collimating lens 28. The collimating lens 28 is arranged between the first spacer 26 and a second spacer 30 and is connected therethrough to a mirror cage 32. These components 20-32 form the excitation assembly 12 that, as will be described, provides excitation light for an imaging process.

The excitation assembly 12 is coupled through a coupling spacer 34 to the filter assembly. As will be described, the filter assembly 14 serves to filter and deliver excitation light to the object being imaged and receive and filter light received from the object being imaged. The filter assembly 14 includes a housing 36 having a plurality of passages 38-44 formed therein. Specifically, the housing has an excitation passage 38 that is configured to receive the coupling spacer 34 to thereby connect the excitation assembly 12 to the filter assembly 14 and receive the excitation light therethrough. The housing 36 also includes an excitation/reception passage 40 that, as will be described, is designed to have both excitation and received light pass therethrough. Arranged opposite the excitation/reception passage 40 is a reception passage 42 that is designed to receive light from the object being imaged. Finally, it is contemplated that an optional passage 44 may be included, in the illustrated configuration, opposite the excitation passage 34. Though not required, the optional passage 44 may be provided to allow for assembly and maintenance purposes or may be used to reconfigure the device 10, such as moving the excitation assembly 12 to the opposing side of the device 10 from that illustrated. Also, it is contemplated that additional optional components may be coupled to the device 10 through the optional passage, for example, fluid management systems and the like that will be described in detail below. If included and unused, it is contemplated that a cover or cap 46 may be provided to close the optional passage 44.

To close the housing 36, a top cover 48 and bottom cover 50 are provided that include a plurality of connection points that are positioned to allow a plurality of elements to be arranged within the housing 36. Specifically, in the illustrated configuration, it is contemplated that three main components may be arranged in the housing 36. First, an excitation filter 52 may be secured within a first filter mounting 54 to be secured within the housing 36 in a position proximate to the excitation passage 38 so as to receive the excitation light from the excitation assembly 12, but not interfere with received light from the object being imaged. Second, a dichromatic mirror 56 is secured in a mirror mounting 58 and positioned relatively centrally within the housing 36 so as to receive both the excitation light provided from the excitation assembly 12 through the excitation passage 38 and received light traveling from the object being imaged through the excitation/reception passage 40. Finally, a reception filter 60 is secured in a second filter mounting 62 and positioned proximate to the reception passage 42 to filter received light, but not excitation light from the excitation assembly 12.

As will be described in greater detail below, at least a first spacer 64 and a second spacer 66 are connected to the excitation/reception passage 40 and hold respective first and second lenses 68, 70 that together form an afocal lens pair. The operation of these components and other optional spacers, optical bundles, and the like that may be connected to the second spacer 66 and second lens 70 will be described.

Referring back to the housing 36, a pair of spacers 72, 74 are connected to the reception passage 42. The later spacer 74 is configured to receive an imaging lens 76 that is arranged proximate to an iris 78. The iris 78 is coupled to a pair of spacers 80, 82 and an adapter ring 84 to which an image capturing device 86 is coupled.

Figure 3:
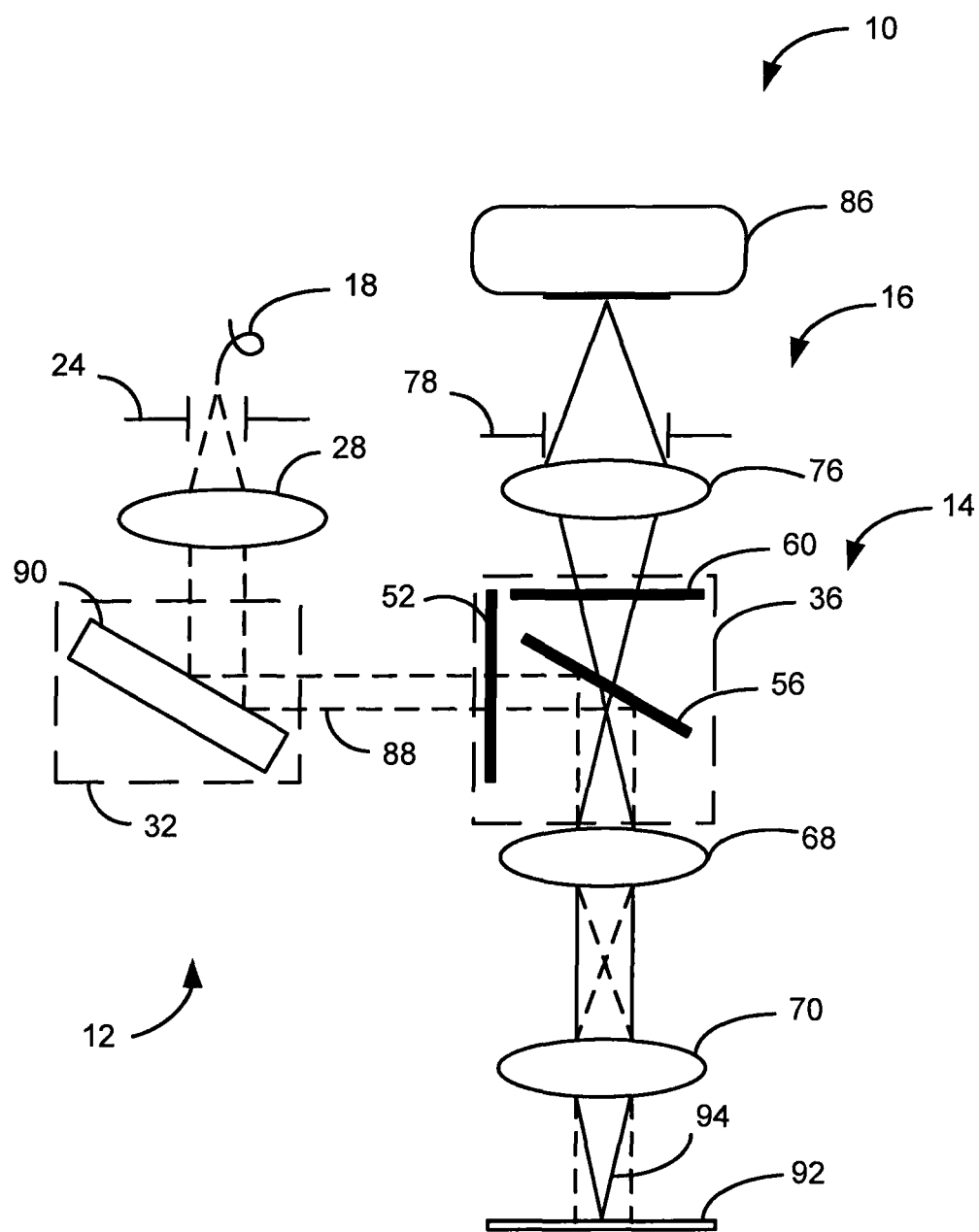
FIG. 3 is a schematic of an exemplary optical assembly of the exemplary device of FIGS. 1 and 2.

Turning to FIG. 3, a portion of the components described above with respect to FIGS. 1 and 2 are illustrated. Specifically, for example, the structural components, such as the adapters, spacers, housing, and the like have been removed to facilitate a discussion of the optics of the device 10. These structural components, as will be described, are, however, quite important to the operation that will be described with respect to FIG. 3. For example, as will be described, the structural components, such as the spacers, are specifically designed to facilitate the advantages yielded by the present invention.

In operation, as described above, excitation light 88 is delivered by the excitation fiber bundle 18 and passes through the iris 24, which reduces extraneous light by forcing the photons to travel on a path that is substantially perpendicular to a plane of the collimating lens 88. It is contemplated that the iris 24 may be manually or automatically controlled to adjust the amount of excitation light 88 utilized. After passing through the iris 24, the collimating lens 28 collimates the excitation light before it enters the mirror cage 32. In the mirror cage 32, a mirror 90 is mounted so as to reflect the excitation light received such that the excitation light passes from the collimating lens 28 and turns ninety (90) degrees to pass through the spacer 34 and excitation passage 38 of the housing 36 of FIG. 2.

Upon entering the housing 36, the excitation light 88 passes through the excitation filter 52. The excitation filter 52 is configured to act as a bandpass filter that restricts the excitation light 88 to a narrow wavelength band to a desired fluorophore absorption characteristic. For example, a 625 nm-680 nm wavelength bandpass filter can be used to excite fluorophores or other optical probes with absorption maxima within that band, such as Cy5.5. The excitation light 88 then impinges the dichromatic mirror 56 and is reflected at a ninety (90) degree angle. As will be described, the dichromatic mirror 56 is designed to reflect the excitation light 88 but allow other selected light to pass therethrough. In certain implementations, one or more of the excitation filter 52, dichromatic mirror 56, and reception filter 60 are interchangeable. In such implementations, the filters and dichroic can therefore be matched with the spectral excitation and emission characteristics of the fluorophore, or other optical probe, used to label the target.

After reflecting off of the dichromatic mirror 56, the excitation light 88 passes through the afocal lens pair 68, 70. As illustrated, the afocal lens pair 68, 70 directs the excitation light 88 in a collimated fashion onto an object being imaged 92. As will be described, depending upon the type of excitation light used, quantum dots and dyes or dyes are utilized and whether such light is used to trigger bioluminescent mechanisms, the delivery of the excitation light 88 may be reflected by the object being imaged 92, may cause the object being imaged to emit light, or the object being imaged may fluoresce. Regardless of the mechanisms utilized, light is received from the object being imaged 92 that is referred to herein as a "received light" 94. For example, the received light 94 may be emitted photons from excited fluorophores, in the case of fluorescent optical probes.

The received light 94 passes through the afocal lens pair 68, 70. It should be noted that the afocal lens pair 68, 70 are designed to not perform any magnification. The received light 94 then passes into the housing 36 were it meets the dichromatic mirror 56. However, unlike the excitation light 88, the dichromatic mirror 56 is configured to allow the received light 94 to pass therethrough and onto the reception filter 60. The reception filter 60 is a bandpass filter that allows transmission of a narrow wavelength band, for example, according to fluorophore emission characteristics. Following the reception filter 60, the received light 94 passes to the imaging lens 76, which relays the image formed by the afocal lens pair 68, 70 through the iris 76, to the image capturing device 86.

It is contemplated that the image capturing device 86 may be any of a variety of photosensitive devices capable of collecting the received light 94. For example, the image capturing device 86 may be a charge coupled device (CCD), an avalanche photodiode (APD), or the like.

The choice between an APD or a CCD array for detection will depend upon the desired illumination and emission characteristics. The primary difference between the APD and CCD detector arrays is that the APD can be run in Geiger mode to yield a very high sensitivity (one photon per second) if desired. For instance, in the event that filters are used to eliminate backscatter from a laser pulse, it may be desirable to utilize the higher sensitivity of the APD. Specifically, the APD can detect weak optical signals due to the internal gain in the detector itself. Because the APD acts as a passively quenched circuit, when it detects single photons an electric field is generated that is sufficiently high to sustain the flow of an avalanche current. Other approaches that rely on external electronic amplification of a weak signal introduce a high background. Additional advantages of the APD include a high quantum efficiency and time resolution, which, if desired, allows temporary gating of the detection and the use of a separate cell auto-fluorescence from probe fluorescence. Because the APDs can count single photons of light, they have the sensitivity to detect single cancer cells that have been activated by the optical probe.

There are a number of performance parameters that affect the sensitivity of the system that stem from the biology of the object being imaged. For example, the number of ligand reactions per second per cell together with the fluorescent duration (milliseconds) gives the number of possible florescent events per second per cell. The pulse rate should be as high as possible, limited by the detector response time, so as to achieve a substantially high photon generation from the molecular probe.

In certain implementations, the disclosed device includes thin optics as focusing elements to reduce the overall mass of the disclosed device and increase its portability. In such implementations, one or more of the lenses may be Fresnel lenses.

As noted above, the afocal lens pair 68, 70 are designed to not perform any magnification. It is contemplated that this is similarly true of the other filtering components, such as the dichromatic mirror 56 and imaging lens 76. Thus, the image received by the imaging device 86 is not magnified or substantially unmagnified. In this regard, it is contemplated that the imaging device 86 serve as an image processor having a field of view (FOV) substantially greater than a diameter of a cell of the object being imaged 92. However, the imaging device is designed to have an analysis resolution substantially matched to the diameter of a cell of the object being imaged 92. In this regard, the received light 94 corresponding to each cell in the FOV is individually analyzed. That is, unlike the prior-art systems described above, the imaging system 10 is capable of analyzing a substantially large volume of tissue simultaneously with sufficient accuracy, such as on an individual cellular level, to provide clinical certainty of tissue pathology in vivo.

Therefore, as described above, the present invention provides a wide FOV with an analysis resolution substantially matched to the size of a cell by matching a given cell with one or more pixels of a CCD or APD array such that the field of view of any pixel is one cell or less. This provides a desirable photon flux rate (photons/sec-area) and desirably controls the background emission (auto fluorescence) which, along with the dark count, determines the signal-to-noise ratio of the instrument and its sensitivity. If the field of view of a pixel contains several cells and only one is a cancer cell that has illuminated molecular probes, the average photon flux rate to the pixel will be reduced and the ratio of the signal-to-background noise will be, likewise, reduced. Furthermore, if multiple cancer cells are closely spaced, the device will still be able to differentiate individual cells.

Optical probes, such as Prosense and particularly Prosense 750, may be used with the above-described system that are activated by enzymes, which are up-regulated in cancer cells. Prosense is a registered trademark of VisEn Medical, Inc. of Bedford Mass. Prosense and Prosense 750 are just one type of optical probe and many biomedical reagents in the nature of contrast media for in vivo imaging of molecular and morphologic targets and processes in humans and animals are within the scope of the present invention.

Such contrast agents can be administered to the patient either via systemic injection before tumor removal or by topical application, such as by "painting" directly over the tumor bed after the cancer has been removed. Target cells will be labeled with such contrast agents by, for example, activation by enzymatic activity, specific recognition of antibody-antigen interaction, and/or surface receptor recognition. In one instance, a variety of multiplexed optical probes can be used, including any combination of these approaches, to improve specificity. In other instances, a variety of multiplexed contrast agents can be used to identify different types of cells, for example metastatic versus non-metastatic, inflammation-related cells, and the like, as well as physiological features, such as formation of vasculature, density of extracellular matrix, and the like.

Turning to the example of Prosense 750, in operation, in the absence of protease activation, Prosense 750 is taken up into cells and quenched by fluorescence resonance energy transfer (FRET). After protease activation, incident light, for example, with a wavelength of 750 nanometers (nm) is absorbed by the probe. The probe then emits light, for example, with a wavelength of 780 nm (a phenomenon called Stoke's shift) so that the tumor can be detected. As described above, the present invention utilizes this variation in wavelength between the excitation light and the received light to discriminate between, excitation light, received light, ambient light, scattered light, and the like. That is, the above-described filter assembly is configured to direct excitation light, such as by reflection off the dichromatic mirror, to the object being imaged. In addition, the above-described filter assembly is configured to direct only desired received light, such as that emitted by a cell being imaged to the imaging device, while reflecting or otherwise rejecting light other than the desired received light. This careful discrimination may be achieved by, for example, only allowing received light having a particular wavelength known to be substantially received from the cells being imaged to pass through the dichromatic mirror.

In laboratory settings, gene expression profiling has been used to identify cathepsin proteases as genes over-expressed in lung cancer in mice. However, using the above described system and an optical probe, such as Prosense 750, primary lung cancers can be directly imaged in three dimensions with fluorescence molecular tomography (FMT). Utilizing the same cathepsin-activated probes, autochthonous sarcomas have been imaged with FMT.

Figure 4:
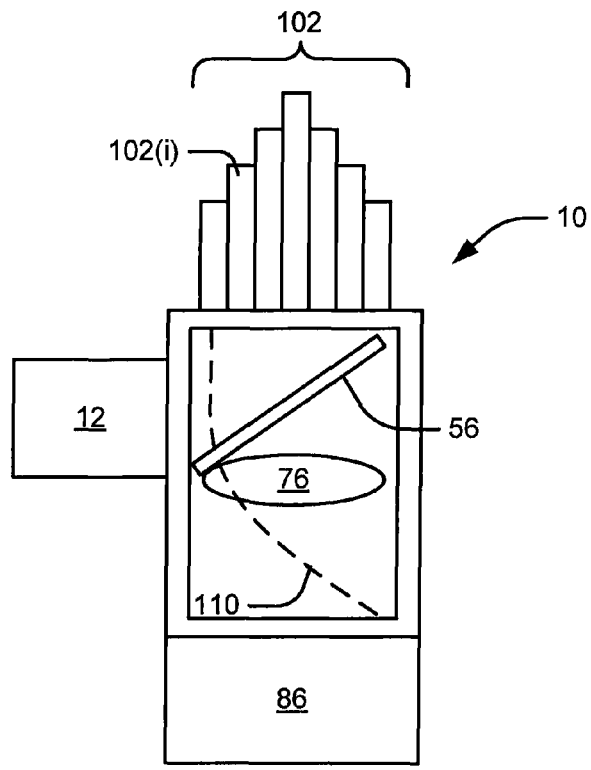
FIG. 4 is a simplified block diagram of an exemplary configuration of a portion of the optical assembly of FIG. 3.

It is contemplated that the above-described system may be advantageously coupled with a variety of additional components. For example, turning to FIG. 4, a block diagram is presented of the basic imaging device wherein a single cell is associated with one or more pixels of a detector. As can be seen in FIG. 4, the simplified representation of the device 10 includes the excitation assembly 12, the imaging lens 76, the dichromatic mirror 56, and an imaging device or detector 86, which has a pixel array (not shown in FIG. 4). As illustrated, a fiber optic bundle 102 may be included that is made of a plurality of individual fibers 102(i).

In the illustrated implementation of FIG. 4, each pixel of the detector 86 is paired with one or more fibers 102(i), thereby limiting the light detected by each pixel to that transmitted by associated fiber(s) 102(i). Thus, the per-pixel FOV of the detector 86 is constrained by the combined diameter of the distal ends of the associated fiber(s) 102(i). By way of example and not limitation, in one implementation of the device 10, the pixel array of the detector 86 includes pixels that are five (5) microns across and spaced five (5) microns apart. If the cells being imaged have a diameter of twenty (20) microns, then approximately every four (4) pixels of the detector 86 could image a single cell. To achieve such a per-pixel FOV, the fibers 102(i) of the fiber optic bundle 102 could be between 2-5 microns.

When used, light from the excitation assembly 12 is reflected ninety (90) degrees by the dichromatic mirror 56 to the base of the fiber optic bundle 102. In the present implementation, the dichromatic mirror 56 may be interchangeable and may be selected to reflect the wavelength of light emitted by the excitation assembly 12 and transmit the wavelength of light emitted, reflected, or fluoresced by the object being imaged.

After being reflected by the dichromatic mirror 56, light from the excitation assembly is transmitted by the fibers 102(i) to a tissue surface. Dashed line 110 illustrates the path of the resulting emitted or reflected light from the applied optical probes through the device 10 and onto the detector 56.

Figure 5:
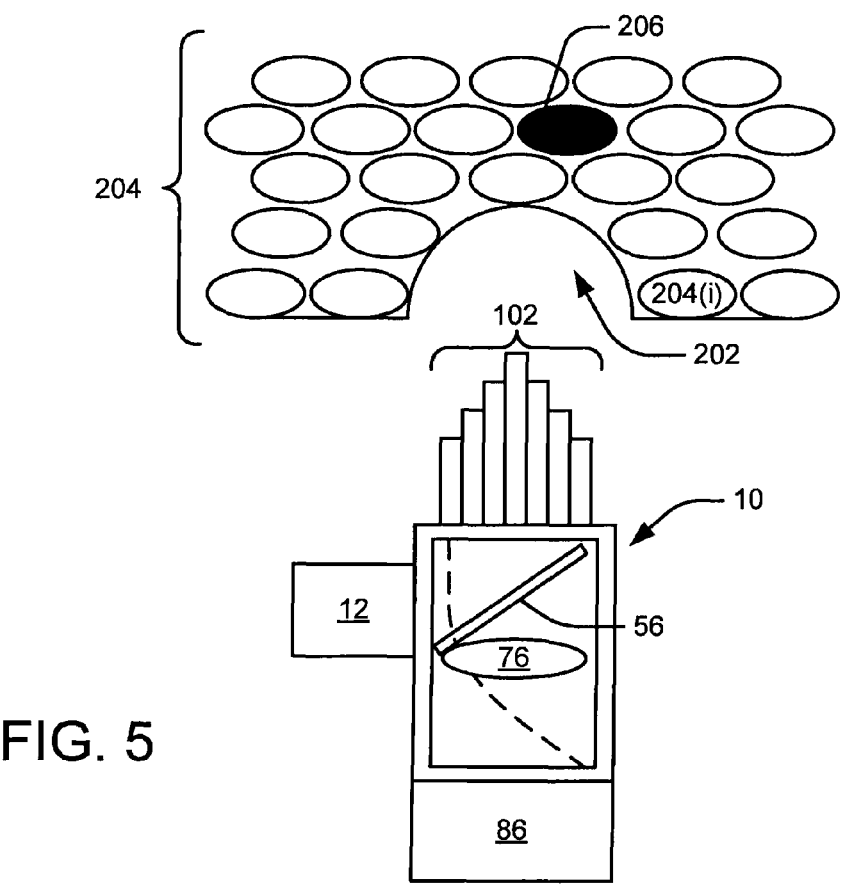
FIG. 5 is a block diagram illustrating an exemplary relationship between a tapered fiber optic bundle of the device of FIG. 4 and a resected area of tissue.

In the illustrated implementation of FIG. 4, the fibers 102(i) have different heights resulting in the fiber optic bundle 102 having a contoured surface. Such an implementation may be desirable for inspecting a resected area after a tumor has been surgically removed. Referring now to FIG. 5, the relationship between a tapered fiber optic bundle 102 and a resected area is illustrated. In FIG. 5, the tissue 204 is illustrated as including healthy cells 204(i) and a cancer cell 206 and having a crater-shaped area of interest 202 having a diameter, by way of example and not limitation, of 1 cm to 5 cm in diameter. As can be seen, the contoured fiber optic bundle 102 is designed to conform to the area of interest 202 thereby providing intimate contact with the tissue 204 in the detection of the exemplary cancer cell 206.

In an implementation where a fluorescent optical probe has been applied to the area of interest 202, the excitation assembly 12 may be used to emit a laser pulse of a first wavelength to excite the fluorescent optical probe on the cancer cell 206. The dichromatic mirror 56 is selected such that it reflects the first wavelength and transmits the wavelength of the emission light from the optical probe. Thus, the emission light enters the fiber optic bundle 102 between pulses from the excitation assembly 12 and travels back through the fiber optic bundle 102 to the dichromatic mirror 56. The emission light passes through the dichromatic mirror 56 and is projected on to the detector 86 by the imaging lens 76.

In certain implementations, the fibers 102(i) have other configurations to match various tissue surfaces. Such configurations may be, by way of example and not limitation, concave, convex, planar, abstract, or asymmetrical.

In additional implementations, the fiber optic bundle 102 acts as in concert with or instead of one or more of the spacers of FIGS. 1 and 2 to keep the imaging lens 76 at a fixed distance from the tissue being imaged. In other implementations, the device 10 uses a different spacer component, including but not limited to, a collar or a solid piece of glass, plastic, or other translucent material. Further guidance on desired spacer configurations will be described below.

Figure 6:
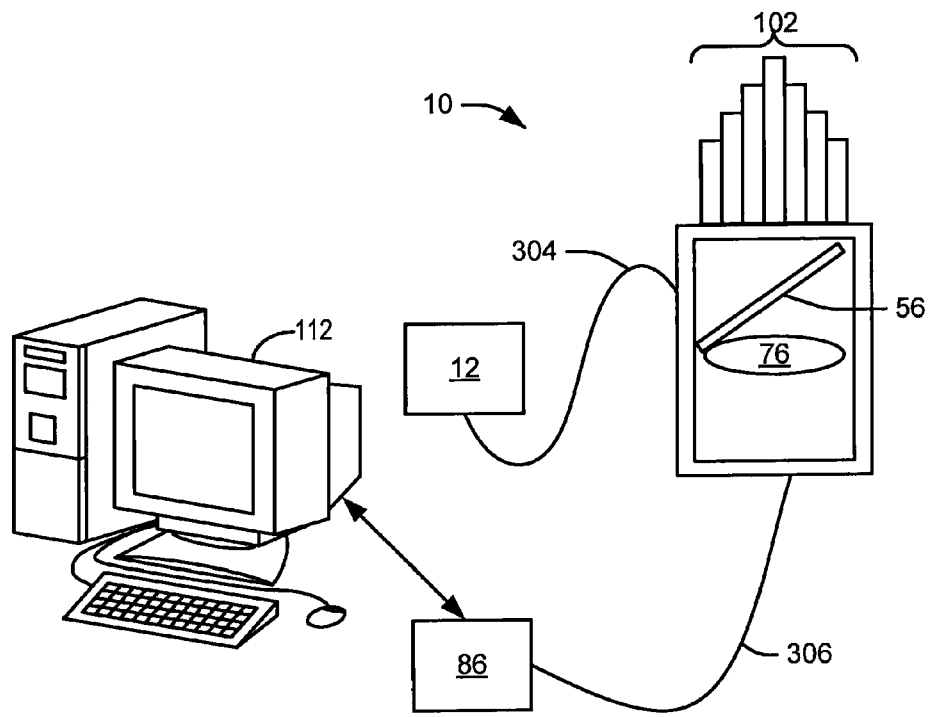
FIG. 6 is a block diagram presenting a one variation of the device depicted in FIG. 4, where a laser and detector are remotely located.

Turning now to FIG. 6, another implementation is presented. In this design, the excitation assembly 12 and assembly 16 are remotely located from the filter assembly 14, which includes the fiber optic bundle 102, the dichromatic mirror 56, and the imaging lens 76. To connect the filter assembly 12 to the excitation assembly 12 and detector 86, a plurality of fiber bundles may be employed. Specifically, a first fiber bundle 304 connects the excitation assembly 12 to the filter assembly 14 and a second fiber bundle 306 connects the detector 86.

The exemplary implementation illustrated in FIG. 6 allows for easier handling of the device 10 by making the device 10 lighter and less cumbersome then other implementations. In certain implementations, the excitation assembly 12 and detector 86 are located in close proximity to the device 10. By way of example and not limitation, they may be located in the same room as device 10. In some cases, the excitation assembly 12 and detector 86 may be located in a separate room where a display and analysis equipment 112 are located.

Figure 7:
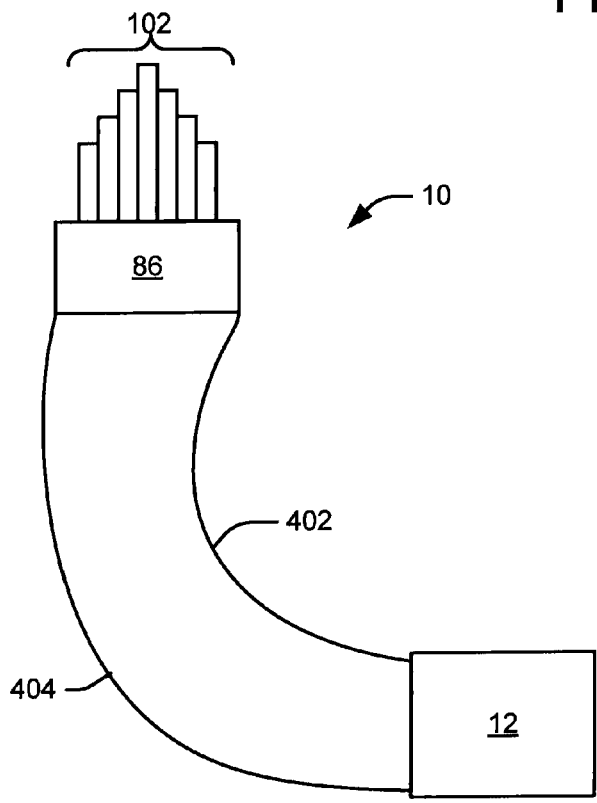
FIG. 7 is a block diagram presenting another variation of the exemplary devices depicted in FIGS. 4 and 6, where a detector or instrument head is in direct contact with the tissue.

The illustrated implementations of FIGS. 4 and 6 both incur some signal loss attributable to the fiber optic transmission and the view factor from a cell to the end of the fiber 102(*i*) as well as from the end of the fiber 102(*i*) to the imaging lens 76. Additional signal loss is caused by the emission light passing through dichromatic mirror 56 and imaging lens 76, as well as other filtering components. Referring to FIG. 7, another implementation for aligning the cells and pixels by direct contact of a detector or an instrument head with the tissue is illustrated, which thereby eliminates some of the signal loss incurred by the implementations of FIGS. 4 and 6.

Figure 8:
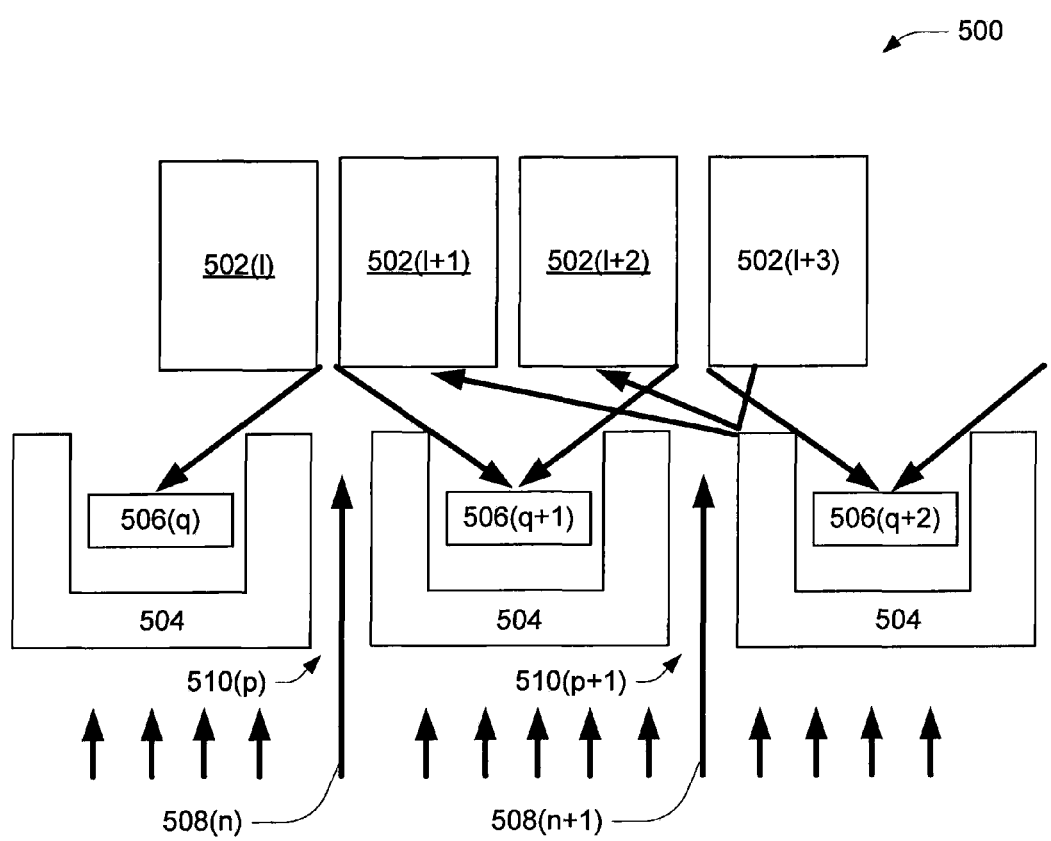
FIG. 8 is a block diagram of an exemplary configuration of the pixels of a detector usable in the exemplary device of FIG. 7.

In the implementation illustrated in FIG. 7, the device 10 includes an instrument head including the fiber optic bundle 102. In this implementation, the pixels of the detector 86 may be interleaved with passages for the light from the excitation source 12 to pass through, as illustrated by FIG. 8. In FIG. 8, excitation light passes through openings 510(*p*) and 510(*p*+1) in a substrate 504 containing pixels 506 of the detector. The excitation light illuminates a plurality of fibers of a fiber bundle 502. Depending on the geometry, each opening 510(*p*) may illuminate one (1) or more fibers 502(*l*). In the present illustration, pixels 506(*q*), 506(*q*+1), and 506(*q*+2) are shown in a cavity within substrate 504. In such an implementation, each pixel 506(*q*) captures emission light transmitted by two (2) of the fibers 502(*l*+*n*).

Figure 9:
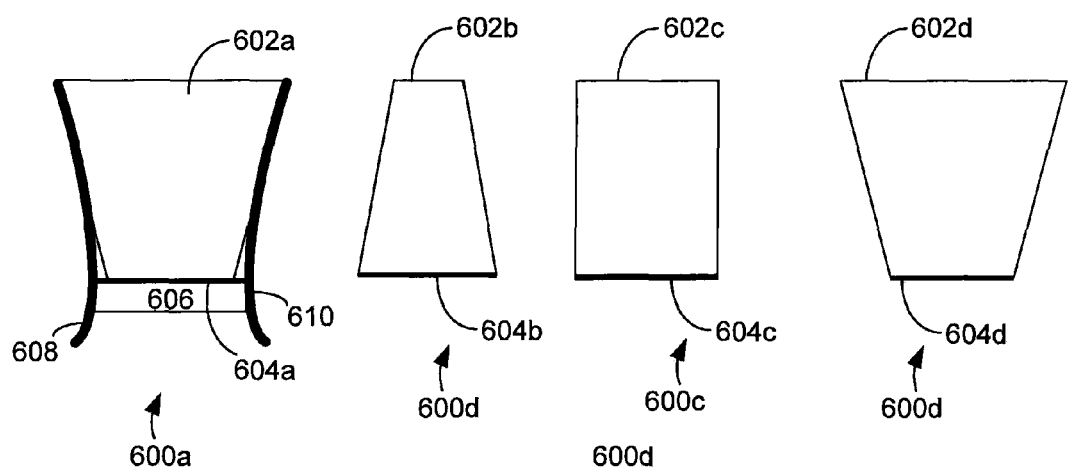
FIG. 9 is an exemplary implementation of a device having a removable, tapered fiber optic bundle coupled to the detector.

Turning now to FIG. 9, yet another implementation for aligning the pixels of the detector with individual cells is provided. As illustrated in FIG. 9, a device 600 includes a removable, tapered fiber optic bundle 602 coupled, through a filter 604, to a CCD or ADP camera 606. Looking first at arrangement 600*a*, a proximal end of a fiber optic bundle 602*a* has an interference filter 604*a* deposited between the fiber optic bundle 602*a* and the detector 600*a* so as to reject back scatter from the excitation source and stray ambient light. The size of the proximal end of the fiber optic bundle 602*a* is such that the individual fibers of the fiber optic bundle 602*a* map to one pixel of the camera 606. This, as will be understood by one of ordinary skill in the art, allows for a quite desirable signal-to-noise ratio. Similarly, the size of the distal end of the fiber optic bundle 602*a* is chosen to map one cell to one fiber, thus resulting in the tapered shape of the fiber optic bundle 602*a*. As can be seen from arrangements 600*b*, 600*c*, and 600*d*, the fiber optic bundles 602*a*, 602*b*, 602*c*, and 602*d* can be tapered in any manner in order to align each fiber with a single pixel at the proximal end and a single cell at the distal end. Further, the size and taper of the various fiber optic bundles can be selected to reach any desired resolution. In one implementation, the fiber optic bundles having differing shapes and tapers are interchangeable. In such an implementation, the FOV, resolution, and observed wavelength can be altered during a surgical procedure by simply fitting a device with a differently shaped fiber optic bundle, a fiber optic bundle that is coupled to a different filter, and/or both.

Returning to device 600*a*, in certain implementations, the emitted light from an excitation assembly could be sent through a separate fiber, such as a fiber 608 and/or a fiber 610. Such an approach further reduces back scatter and increases the ease with which the excitation wavelength can be altered to match different optical probes.

In certain implementations, a single tapered fiber optic bundle is connected to multiple detectors, each detector being side-by-side to each other. Such an implementation further increases the FOV of the disclosed device.

As will be understood by those of ordinary skill in the art, for light to be bound by an optical fiber, the light must enter the fiber at an angle to the fiber's axis that is less than the acceptance angle. Light that falls within the acceptance angle is confined to the core of the optical fiber by total internal reflection, and is therefore guided within the optical fiber's length. The acceptance angle for emission light from the optical probe is dependent upon the numerical aperture of the fiber optic bundle and associated lenses, if any. Additionally, as target cells may be located some distance below the tissue surface, it is unlikely that the tips of all the individual fibers within the fiber optic bundle will be in direct contact with a target cell, thereby affecting the FOV of a fiber and related pixel. As surface irregularities are likely to create an additional gap between a fiber tip and the tissue surface, the total gap between the fiber tip and a cancer cell is preferably between 100-200 microns. This gap widens the FOV of each pixel, adversely affecting the photon density and thus decreasing the sensitivity of the detector.

Figure 10:
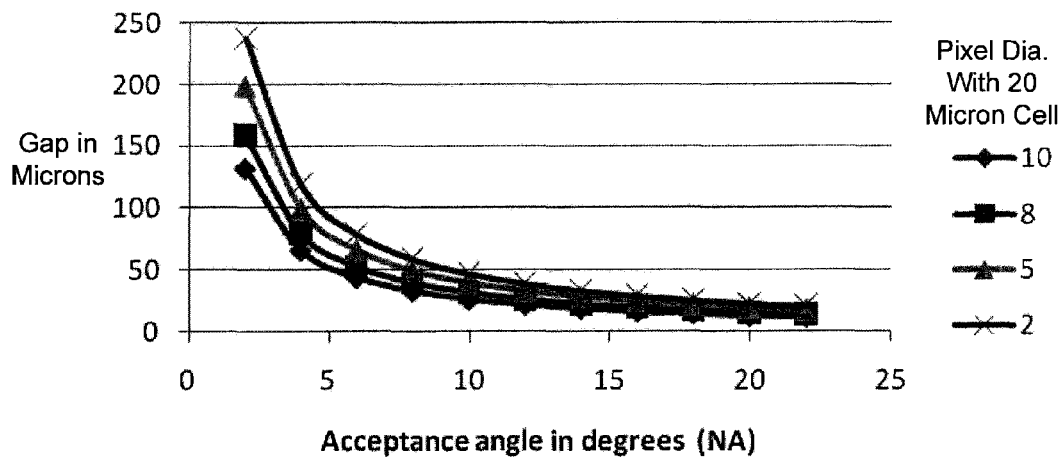
FIG. 10 is a graph illustrating a desirable gap, measured from a fiber tip to a target cell, for a given acceptance angle before which the sensitivity of a detector is substantially decreased.

Referring to FIG. 10, a graph is provided that illustrates the variance in desirable gap, measured from a fiber tip to a target cell, for a given acceptance angle before which the sensitivity of the detector is substantially decreased. As can be seen, larger gaps are tolerated at smaller acceptance angles. By way of example and not limitation, a typical cancer cell may be several microns (50-70 microns) beneath the tissue surface. Thus, as shown in FIG. 10, to lessen the likelihood that individual pixels in the FOV will be larger then a single cell, the acceptance angle should be restricted to five (5) degrees or less.

Figure 11:
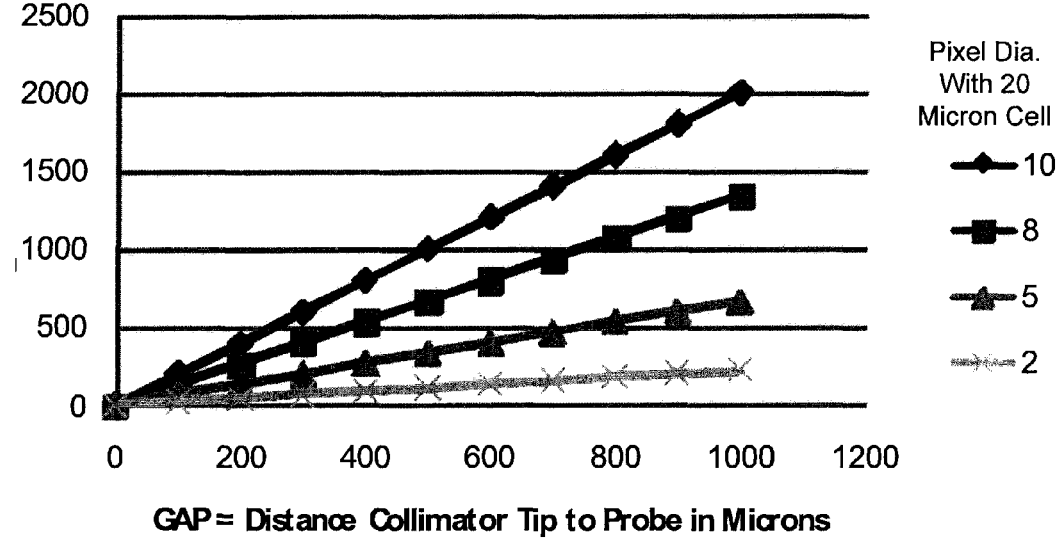
FIG. 11 is a graph illustrating a height of a collimator desired to restrain the per pixel FOV to a single cell or less for gaps of up to 1000 microns.

To counter the effect of a gap on the acceptance angle, and therefore the sensitivity of the detector, a collimator may be used to limit the given pixel to a single cell or less. As will be understood by one of ordinary skill in the art, a collimator narrows light transmitted through it. Referring to FIG. 11 a graph illustrating the heights of collimator designs that are desirable to restrain the per pixel FOV to a single cell or less for gaps of up to 1000 microns. By way of example and not limitation, for a 1000 micron gap, a collimator of 200-500 microns in height is appropriate where the diameter of the emitted light is approximately 2 pixels.

Figure 12:
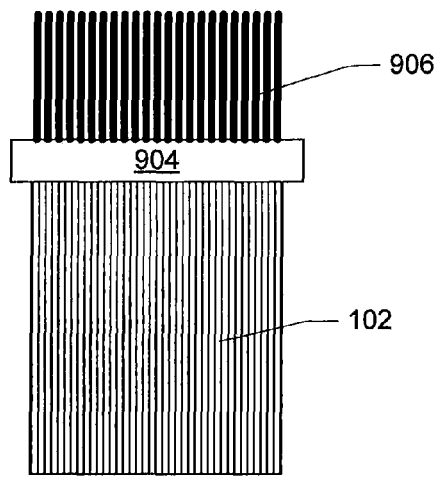
FIG. 12 is a block diagram illustrating an exemplary use of a collimator with a fiber optic bundle to confine the per pixel FOV.
Figure 13:
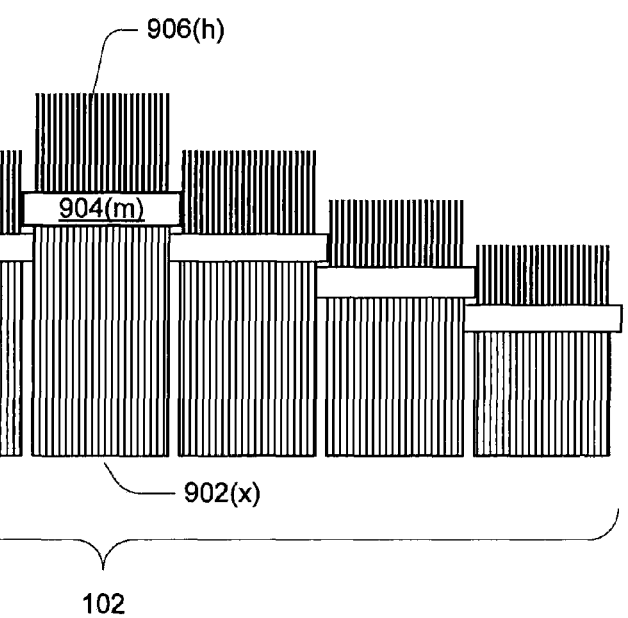
FIG. 13 is a cross-sectional view of an exemplary tapered fiber bundle having multiple collimators.

Turning to FIG. 12, a block diagram is provided that illustrates an exemplary collimator system for use with a fiber optic bundle to confine the per pixel FOV. As shown, a collimator 906 is affixed to the end of fiber optic bundle 102 by a thin end cap 904. As will be known to one of ordinary skill in the art, the length and diameter of the collimator passages is determined by the optical components of the device. To extend the system of FIG. 12 to a plurality of fibers, as illustrated in FIG. 13, a plurality of collimators are utilized and associated with each fiber in the fiber optic bundle 102. As stated previously, the fiber optic bundle 102 may include a taper and, thus, uniform collimator dimensions may be utilized to maintain the contoured configuration. As can bee seen, a series of collimators 904(H) are attached to sections 902 of the fiber optic bundle 102.

Figure 14:
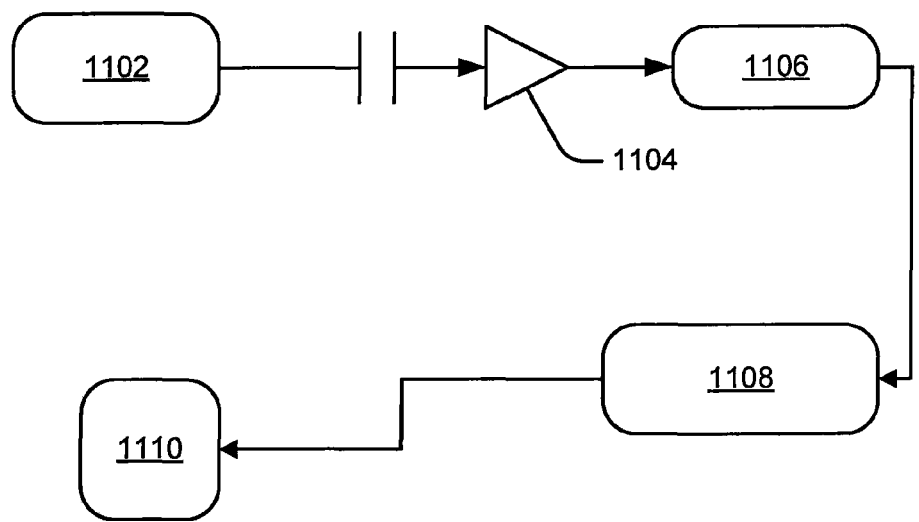
FIG. 14 is a block diagram of an exemplary image stabilization system for use with the disclosed device.
Figure 15:
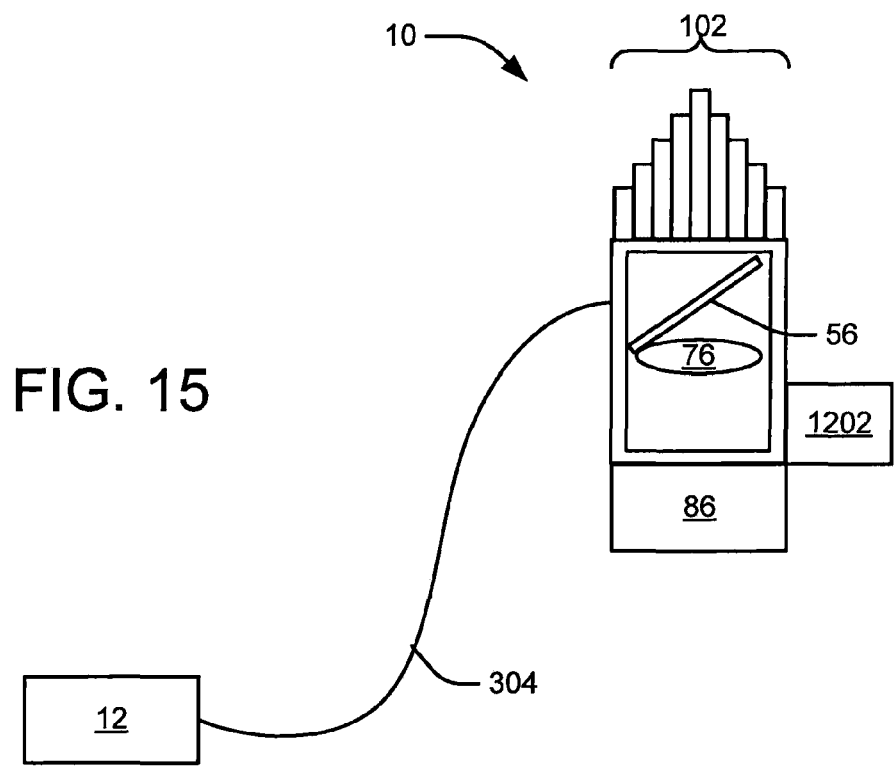
FIG. 15 illustrates the use of the exemplary image stabilization system of FIG. 14 with the disclosed device.

In certain applications, it is desirable to use a stabilization system to maintain a relatively steady image. Referring to FIG. 14, a block diagram of an exemplary image stabilization system for use with implementations of the disclosed device is provided. In the illustrated implementation of FIG. 14, motion is detected by a dual-axis gyroscope 1102. The signal is then amplified by an amplifier 1104 and is processed by an analog-to-digital converter (ADC) 106. In certain implementations the signal is further processed by a digital signal processor (DSP). The signal is then used to initiate an integrated motor drive 1108 and lens motor 1110 to adjust the focus. Such systems are well known in the video arts and can be readily applied to the present design by those of skill in the art. As shown in FIG. 15, in a hand-held implementation of the disclosed device, an image stabilization module 1202 can be integrated with the filter assembly 14.

In certain implementations, it is desirable to use the disclosed device in connection with an integrated fluid management system. Tissue fluids, such as and without limitation, blood, serum, and interstitial fluids, can collect at the detection site. This fluid can scatter the light from the optical probes, limiting the sensitivity of the disclosed device. Further, it may be necessary to provide various reagents to the detection site to conduct the assay.

Figure 16:
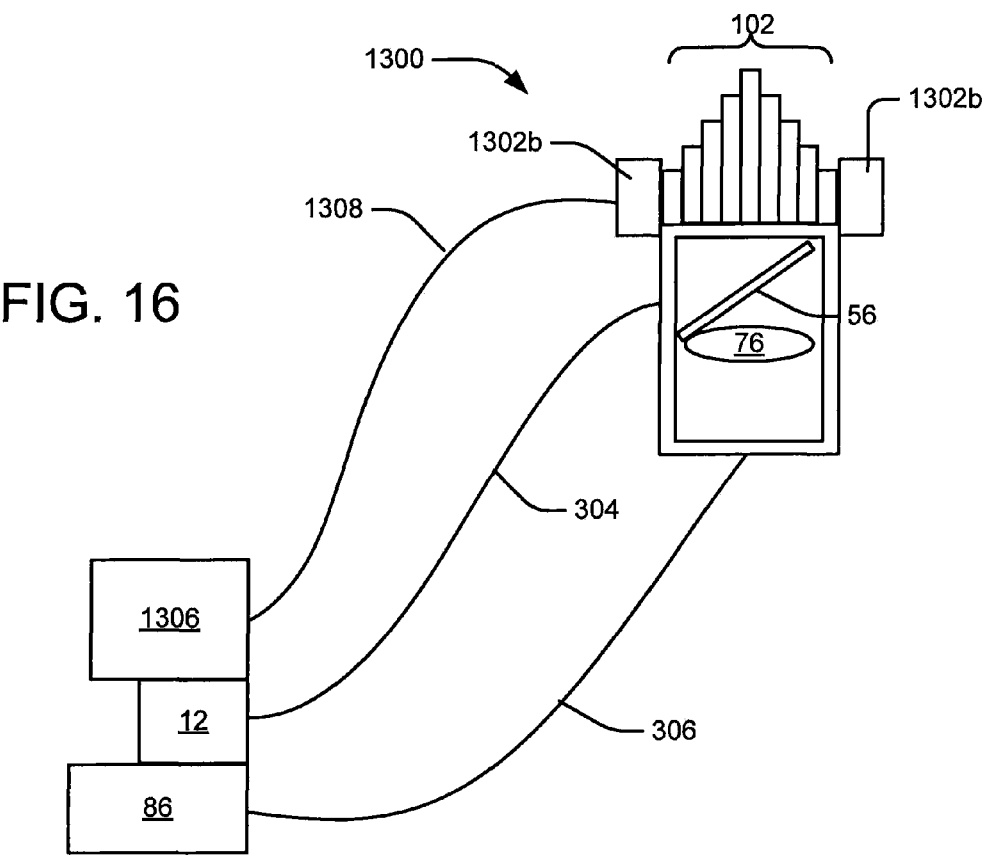
FIG. 16 is a cross-sectional view of the disclosed device with an exemplary integrated fluid management system.

Turning to FIG. 16, a device 1300 is depicted with an exemplary integrated fluid management system that includes a fluid management unit 1306, a connection tube 1308, and a distribution unit 1302 surrounding the fiber optic bundle 102. As will be understood by one of ordinary skill in the art, as FIG. 16 is a cross-sectional view of device 1300, the distribution unit 1302 is depicted as two parts, 1302*a* and 1302*b* to either side of the fiber optic bundle 102.

In certain implementations, the fluid management unit 1306 can remove liquids at the detection site using either suction to collect the liquid or air to push it away. In such an implementation, the suction or air would be pumped by the fluid management unit 1306 through the connection tube 1308 to the distribution unit 1302.

In other implementations, the fluid management unit 1306 is used for local application of the optical probe. The fluid management unit 1306, in such implementations, may contain the optical probe, which is transferred to the distribution unit 1302 by the connection tube 1308. The distribution unit 1302 then delivers the optical probe to the surface of the detection site.

Figure 17:
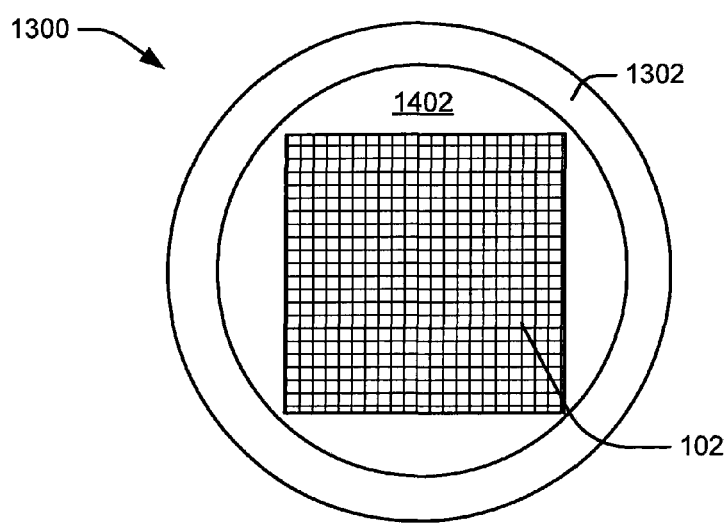
FIG. 17 is an overhead-view of the integrated fluid management system of FIG. 16.

To better understand the configuration of the distribution unit 1302 and the fiber optic bundle 102, FIG. 17 presents a plan view of the distal end of the device 1300. Fluid, in either gaseous, liquid, or vapor form, is either drawn away or delivered to the detection site by a delivery path 1402 surrounding the fiber optic bundle 102 disposed inside of the distribution unit 1302.

Figure 18:
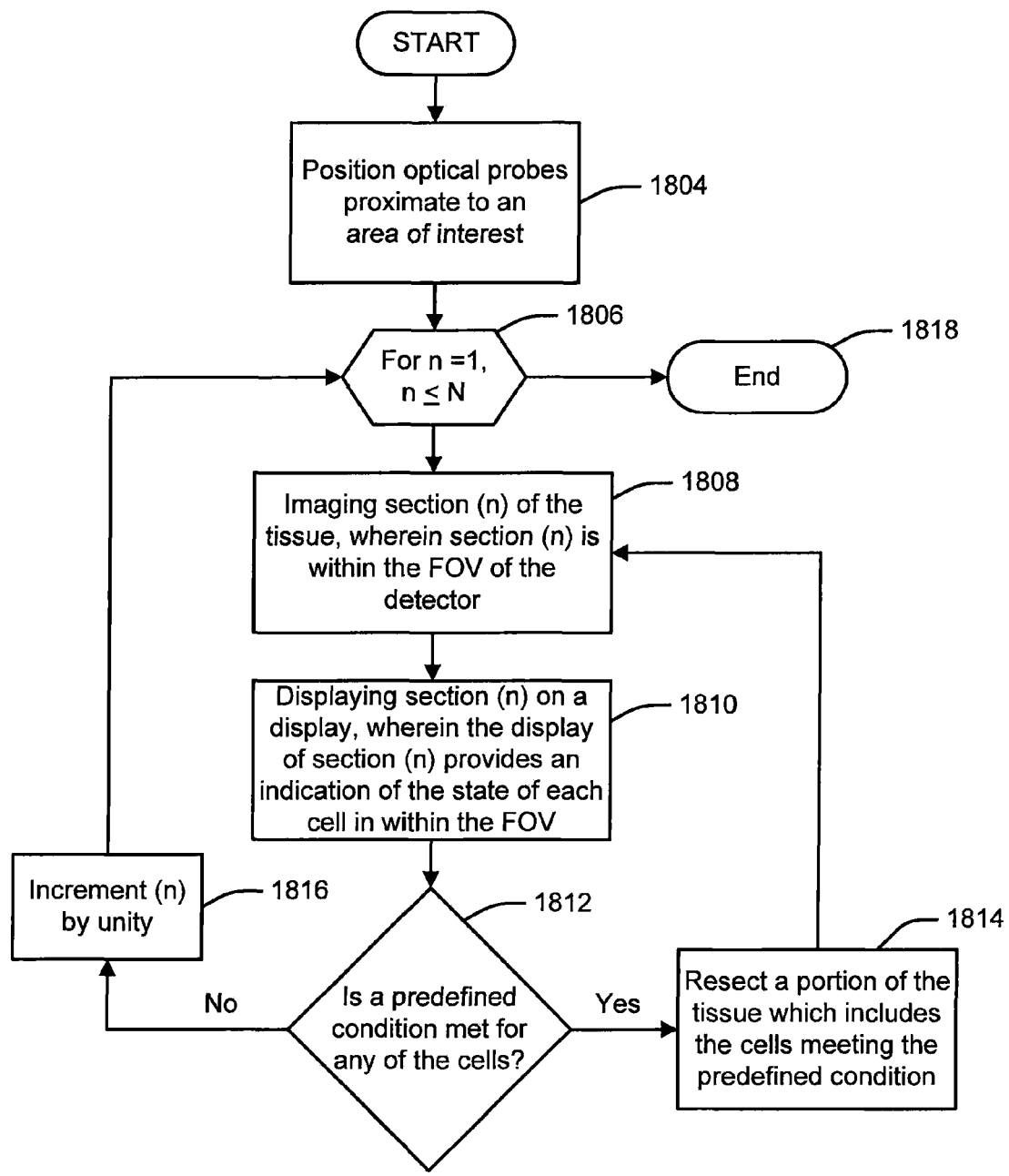
FIG. 18 is a flowchart setting forth the steps of an exemplary method of using the disclosed device to intra-operatively identify target cells in-vivo.

Turning now to FIG. 18, a flowchart of an exemplary method is presented for intra-operatively using a wide FOV, single cell analysis system as described for in-vivo examination. In particular, after a cancerous tumor is removed from a patient, the process for using a wide FOV, single cell imaging system begins by positioning the probe proximate to the area of interest, as indicated at process block 1804. In certain implementations, the medical imaging system provided includes a fluid management system capable of delivering the optical probes. In other implementations, the optical probes are delivered using another device. In certain implementations, the optical probes are fluorophores. In other implementations, the optical probes use luciferase, FRET based, quantum dots, dyes, or any other type of optical probe, or combination thereof.

Once the device is placed in contact with the tissue within the area of interest, each section (n), where section (n) is the portion of the tissue within the FOV of the medical imaging system, is imaged as indicated by blocks 1806, 1808, and 1810. In particular, as indicated by block 1810, section (n) is displayed, providing an indication of the state of each cell within the FOV. In certain implementations, section (n) is displayed on a monitor. In such implementations, the monitor may be connected to a computer having image analysis software stored thereon. In other implementations, the display may be a viewer located on the medical imaging system itself. In yet other implementations, the display may be remotely located from the medical imaging system.

In certain implementations, the cells displayed are color coded to indicate their state. In such implementations, each cell that is interacting with an optical probe may be assigned a color based upon the intensity of energy detected. In such an implementation, other cells may be depicted in a gray scale or may not be displayed at all.

As indicated by blocks 1812 and 1814, if a predefined condition is met for any of the cells, a portion of the tissue containing the target cells is removed, thereby transforming the remaining area by leaving it clean of target cells. In certain implementations, the predefined condition indicates that a cell is cancerous. In such an implementation, the predefined condition may be that the intensity of energy detected from the cell meets a threshold. In other such implementations, the predefined condition may be that the radiation detected from the interaction between the target cell and the optical probe is of a particular wavelength. In other implementations, the predefined condition may be a combination of such factors.

Once the tissue containing the target cells has been removed, the same section (n) is imaged and inspected for remaining cells meeting the predefined condition, as indicated by blocks 1808, 1810, and 1812. In certain implementations, this process is repeated until no cells within section (n) meet the predefined criteria.

Where the predefined condition is not met, (n) is incremented by unity or one (1), as indicated by block 1816, and the processes described in connection with blocks 1808, 1810, 1812, and 1814 are repeated until each section (n) has been inspected for target cells.

In certain implementations, only a sampling of sections of the tissue may be inspected for target cells. Such an implementation may be employed where the area of tissue to be inspected is quite large or where a given number of sample sections adequately describe the entire area of interest.

In certain implementations, each section (n) may be inspected before any tissue is resected. In such an implementation, analysis software or other means may be employed to create a map or otherwise maintain a reference of those sections containing cells meeting the predefined criteria. In such an implementation, those areas having cells meeting the predefined condition may then be resected at the same time, and the sections may again be inspected. In other implementations, a layer of tissue from the entire area of interest may be removed.

In certain implementations, rather then performing an in-vivo inspection, the resected tissue, including the tumor, is inspected in-vitro. In such an implementation, the removed tissue is inspected to determine if the margin surrounding the tumor is clean. That is, that the tumor is surrounded by a layer of healthy tissue. In such implementation, the entire surface area of the removed tissue may be inspected. In other such implementations only a sampling of representative sections of the tissue may be inspected. In such implementations, if target cells are identified in the margin of tissue surrounding the tumor, a layer of tissue from the tumor site may be removed.

Fiduciary markers may be used to help a surgeon identify areas for further resection. For example, in order to provide spatial reference to the user for precisely locating displayed images on to the actual tumor bed, fiduciary markers can be placed at different locations over the inspection area. These markers can be placed before the initial removal of the main tumor, after removal of the main tumor, or during the imaging phase of the surgery. The fiduciary markers can be removed after surgery or made of a biodegradable, biocompatible material that will be naturally dissolved by the patient's body. In other such implementations, rather than using markers, a record may be made of the location. In other implementations, it may not be possible to safely remove the identified target cells due to the cells' proximity to other structures. In such implementations, targeted radiation treatment may be performed intra-operatively. In other implementations, markers may be inserted that can later be used to identify the area containing the target cells for targeted post-operative radiation treatment.

Figure 19:
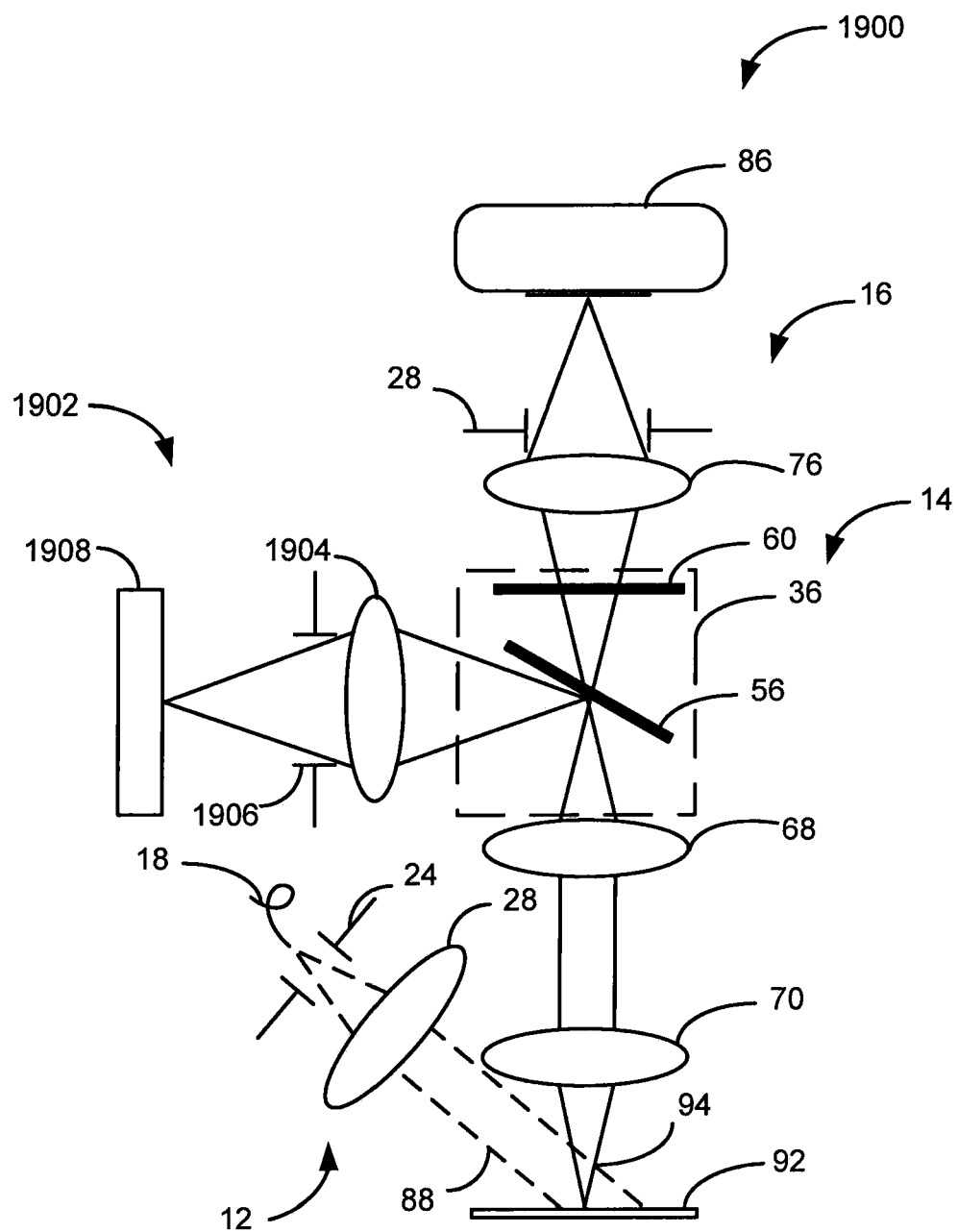
FIG. 19 is a schematic of an exemplary optical assembly of a variation of the exemplary device of FIGS. 1 and 2.

Referring now to FIG. 19, a schematic of an exemplary optical assembly 1900 that is varied slightly from that of FIG. 3 is shown. Generally speaking, the optical assembly 1900 is substantially similar to that described with respect to FIG. 3 and, thus, like components have been numbered alike. However, the illustrated configuration includes a second imaging assembly 1902 and the excitation assembly 12 has been decoupled from the filter assembly 14. The second imaging assembly 1902 includes an imaging lens 1904, a third iris 1906, and second imaging device 1908. In operation, the excitation assembly 12 excites object being imaged 92. As illustrated, the excitation assembly 12 may be decoupled from the filter assembly 14; however, in some configurations, the excitation assembly 12 may remain coupled to the filter assembly 14. In the manner described above, received light 94 is captured by the filter assembly 14 and delivered to the imaging assembly 16. However, in the illustrated configuration, the dichromatic mirror 56 does not simply reject light outside of the desired bandwidth for imaging by the first imaging device 86. Instead, light in a second bandwidth is directed toward the second imaging assembly 1902 where it is focused by the imaging lens 1904, constrained by the third iris 1906, and processed by the second imaging device 1908 to create a second image. It is noted that, for example, additional filtering, such as provided by excitation filter 52 are not necessarily needed in this configuration. Rather, the dichromatic mirror 56 may be configured to act as a long-pass filter, whereby white light is reflected to the second imaging assembly 1902 and near infrared (NIR) light is transmitted to the first imaging assembly 16. Of course, one of ordinary skill in the art will readily appreciate that other bandwidths and configurations are readily applicable.

With the system described above with respect to FIG. 19, the two image capturing devices, which may be CCDS, CMOS, or the like, can be used to provide a reflectance color image of the inspection area generated with white light and a fluorescence image of the same inspection area generated with the NIR light. The color image may be used to provide a visual reference to the user, while the fluorescence image may be used to provide information about the presence or absence of cancerous cells. In some instances, it may be desirable to display the two images side by side on a screen. In other instances, the fluorescence image may be overlaid onto the color image to allow for rapid identification of the location of cancer cells with reference of the tumor bed.

Therefore, a device has been described for imaging individual cells over an FOV of, for example, between 0.5-10 cm. The presented device can be hand-held and is intended for intra-operative use, both in-vitro and in-vivo, to detect individual cells labeled by an optical probe. As will be understood by a person of ordinary skill in the art, an optical probe enables the identification of a target cell via the interaction between the cell and the optical probe.

Although the invention is discussed primarily in connection with the use of fluorescent optical probes, it should be understood that the invention is not so limited in its application. As will be understood by a person of ordinary skill in the art, other optical probes can be used with the presented device, such as and without limitation, bioluminescent, quantum dots, and dyes. In certain implementations, a variety of multiplexed optical probes are used to improve specificity by both phenotype and genotype.

To enable the stated characteristics, the device disclosed herein associates a single cell with one or more pixels of a detector, such as and without limitation, a charge coupled device (CCD), an avalanche photodiode (APD), or other photodetector, thus achieving in a per pixel FOV of a single cell or smaller. This level of resolution provides a desirable photon flux rate (photons/sec-area) and reduces the background emission (e.g., auto fluorescence) which, along with the dark count, determines the signal-to-noise ratio and sensitivity of the device.

The present invention may be embodied in other specific forms without departing from its spirit or essential characteristics. The described implementations are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A medical imaging system comprising:
an excitation source configured to emit an excitation light towards an object having a plurality of cells that at least one of emit, reflect, and fluoresce light in response to the excitation light;
an optical receptor configured to receive the light from the object;
a filter assembly configured to receive the light from the optical receptor and filter the light;
an image detector having a field of view (FOV) substantially greater than about a diameter of a human cancer cell and configured to have an analysis resolution less than or equal to about the diameter of the human cancer cell, wherein the image detector is further configured to receive the filtered light from the whole FOV simultaneously at the analysis resolution through the filter and analyze the filtered light corresponding to each cell in the FOV, wherein the light received by the image detector is at least one of substantially unmagnified and not magnified; and
a feedback system configured to provide an indication of a cell state and a location in the FOV at the analysis resolution for each cell in the FOV meeting a predetermined condition, wherein the predetermined condition is a threshold light intensity.

2. The system of claim 1 wherein the image detector comprises a plurality of pixels and wherein a size of each pixel is substantially matched to the analysis resolution and wherein the image detector is configured to analyze the filtered light associated with each pixel to determine whether a cell in the FOV meets the predetermined condition.

3. The system of claim 1 wherein the filter assembly includes a spectral filter set configured to direct excitation light from the excitation source through the optical receptor to the object and configured to direct light received from the object toward the image detector.

4. The system of claim 3 wherein the filter assembly includes a dichromatic filter including a dichromatic mirror configured to reflect the excitation light to direct excitation light through the optical receptor and configured to allow light received from the object to pass therethrough toward the image detector.

5. The system of claim 1 wherein the optical receptor includes a plurality of optical fibers and wherein a diameter of each optical fiber is less than or equal to about the diameter of the human cancer cell.

6. The system of claim 5 further comprising a spacer assembly configured to maintain a desired distance between a tip of the plurality of optical fibers and the object.

7. The system of claim 6 wherein the spacer assembly includes a disposable tip.

8. The system of claim 6 wherein the desired distance is approximately 100-200 microns.

9. The system of claim 5 further comprising a collimator coupled to the plurality of optical fibers to restrict light received by each optical fiber to an area having a size that is less than or equal to about the diameter of the human cancer cell.

10. The system of claim 1 wherein the analysis resolution is between about 15 to 20 microns.

11. The system of claim 1 further comprising a skirt for isolating an analysis region proximate to the optical receptor from ambient light.

12. The system of claim 1 wherein the filter assembly includes an iris configured to allow user selection of an amount of filtered light delivered to the image detector.

13. The system of claim 1 wherein the optical receptor has a contour configured to substantially match a contour of an in vivo resection site of the object.

14. The system of claim 13 wherein the optical receptor includes a plurality of optical fibers having varied lengths configured to match the contour of the in vivo resection site of the object.

15. The system of claim 1 wherein the excitation source includes at least one of a white light source and a laser and is located remotely from the optical receptor.

16. The system of claim 1 wherein the cell state includes a cell being cancerous.

17. The system of claim 1 further comprising a fluid control system configured to reduce an amount of fluid proximate to at least a portion of the object within the FOV.

18. The system of claim 1 wherein the image detector includes at least one of a charge coupled device (CCD) and an avalanche photodiode (APD) having a pixel size less than or equal to about the diameter of the human cancer cell.

19. The system of claim 1 wherein the excitation source is further configured to activate an optical probe to at least one of emit, reflect, and fluoresce light, and wherein the filter assembly is further configured to distinguish the light from the optical probe from light from the plurality of cells.

20. The system of claim 19 wherein the optical probe includes a biomedical reagent configured to act as a contrast media for in vivo imaging of molecular and morphologic targets and processes of the object.

21. The system of claim 1, wherein the human cancer cell has a diameter greater than 2 microns and equal to or less than about 20 microns.

22. The system of claim 1, further comprising an imaging device configured to collect a color image of the object.

23. The system of claim 22, wherein the feedback system superimposes the cell state indication for each cell with the color image.

24. The system of claim 1, wherein the human cancer cell has a diameter greater than 2 microns and equal to or less than about 20 microns.

25. A medical imaging system comprising:
an excitation light source configured to emit an excitation light towards an object having a plurality of cells that at least one of emit, reflect, and fluoresce light in response to the excitation light;
an optical fiber bundle configured to receive light from the object, each optical fiber in the optical fiber bundle having a diameter that is less than or equal to about a diameter of a human cancer cell;
an image detector having a field of view (FOV) substantially greater than the diameter of the human cancer cell and configured to have an analysis resolution substantially matched to a size of the optical fibers in the optical fiber bundle and further configured to receive the light from each optical fiber of the whole optical fiber bundle simultaneously and analyze the light, wherein the light received by the image detector is at least one of substantially unmagnified and not magnified; and
a feedback system configured to provide an indication of a cell state and a location in the FOV for each cell in the FOV meeting a predetermined condition, wherein the predetermined condition is a threshold light intensity.

26. The system of claim 25 wherein the image detector includes a plurality of pixels and wherein a pixel size of the plurality of pixels is substantially matched to the analysis resolution.

27. The system of claim 25, further comprising an imaging device configured to collect a color image of the object.

28. The system of claim 27, wherein the feedback system superimposes the cell state indication for each cell with the color image.

29. A medical imaging system comprising:
an excitation light source configured to emit an excitation light towards an object having a plurality of cells;
a photosensitive device including a plurality of pixels configured to simultaneously collect light from the object that is at least one of emitted, reflected, and fluoresced in response to the excitation light, wherein a pixel size of the plurality of pixels is less than or equal to a size of a human cancer cell, and, wherein the light collected by the photosensitive device is at least one of substantially unmagnified and not magnified;
a computer configured to identify pixels with light intensities greater than or equal to a predetermined threshold light intensity corresponding to a cell state; and
a feedback system configured to provide an indication of the cell state and location of pixels having light intensities greater than or equal to a predetermined threshold light intensity.

* * * * *